United States Patent [19]

Tsuruta et al.

[11] Patent Number: 4,992,360
[45] Date of Patent: Feb. 12, 1991

[54] SILVER HALIDE LIGHT-SENSITIVE PHOTOGRAPHIC MATERIAL CONTAINING A NOVEL YELLOW COUPLER

[75] Inventors: Mayumi Tsuruta; Noboru Mizukura; Satoshi Nakagawa, all of Hino, Japan

[73] Assignee: Konica Corporation, Tokyo, Japan

[21] Appl. No.: 351,267

[22] Filed: May 11, 1989

Related U.S. Application Data

[63] Continuation of Ser. No. 112,779, Oct. 22, 1987, abandoned.

[30] Foreign Application Priority Data

Nov. 12, 1986 [JP] Japan .................. 61-269216

[51] Int. Cl.$^5$ ................................. G03C 7/36
[52] U.S. Cl. .................... 430/556; 430/557
[58] Field of Search ................. 430/556, 557

[56] References Cited

U.S. PATENT DOCUMENTS

| | | | |
|---|---|---|---|
| 3,658,544 | 4/1972 | Iwama et al. | 430/556 |
| 4,133,958 | 1/1979 | Bore et al. | 430/557 |
| 4,286,053 | 8/1981 | Ishikawa et al. | |
| 4,356,258 | 10/1982 | Usui et al. | 430/557 |
| 4,579,816 | 4/1986 | Ohlschlager et al. | |
| 4,614,709 | 9/1986 | Sasaki et al. | 430/557 |
| 4,745,049 | 5/1988 | Ohbayashi et al. | |
| 4,745,050 | 5/1988 | Seto et al. | |

FOREIGN PATENT DOCUMENTS

| | | |
|---|---|---|
| 0169458 | 5/1986 | European Pat. Off. |
| 3602649 | 7/1986 | Fed. Rep. of Germany |
| 2442464 | 6/1980 | France |
| 2066811 | 7/1981 | United Kingdom |

Primary Examiner—Paul R. Michl
Assistant Examiner—Mark R. Buscher
Attorney, Agent, or Firm—Frishauf, Holtz, Goodman & Woodward

[57] ABSTRACT

A silver halide light-sensitive photographic material comprising a support and, provided thereon, at least one silver halide emulsion layer containing a dye-forming coupler of Formula [I]:

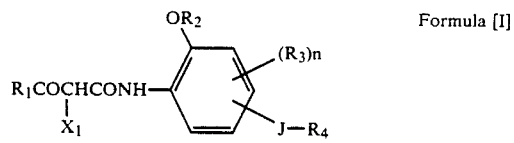

wherein $R_1$ is an alkyl group or a cycloalkyl group; $R_2$ is an alkyl group, a cycloalkyl group, an acyl group or an aryl group; $R_3$ is a group which is substituted to a benzene ring; n is an integer of zero or 1; $R_4$ is an organic group containing one linkage group containing a carbonyl unit or a sulfonyl unit; J is a

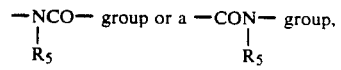

wherein $R_5$ is a hydrogen atom, an alkyl group, an aryl group or a heterocyclic group; and $X_1$ is a group capable of being split off upon reaction with the oxidation product of a color developing agent.

8 Claims, No Drawings

SILVER HALIDE LIGHT-SENSITIVE PHOTOGRAPHIC MATERIAL CONTAINING A NOVEL YELLOW COUPLER

This application is a continuation of application Ser. No. 07/112,779, filed Oct. 22, 1987, now abandoned.

FIELD OF THE INVENTION

The present invention relates to a silver halide light-sensitive photographic material, and more particularly to a silver halide light-sensitive photographic material which uses a novel two-equivalent-type yellow coupler which is excellent in the color formability and produces little or no fog.

BACKGROUND OF THE INVENTION

In the photographic field, two-equivalent-type couplers are now in general use in respect that they enable to obtain maximum dye densities and photographic sensitivities with a small amount of silver. In the case of two-equivalent-type yellow couplers, there are known, as the active site substituent thereto, for example, those aryloxy groups as disclosed in Japanese Patent Publication Open to Public Inspection (hereinafter referred to as Japanese Patent O.P.I. Publication) No. 87650/1974 and U.S. Pat. No. 3,408,194; those oxazolyloxy groups as disclosed in Japanese Patent O.P.I. Publication No. 131325/1976, those chroman-4-oxy groups as disclosed in Japanese Patent O.P.I. Publication No. 139333/-1976; those tetrazolyloxy groups as disclosed in Japanese Patent O.P.I. Publication No. 43426/1977; those 5-pyrazolyloxy groups as disclosed in Japanese Patent O.P.I. Publication No. 150631/1977; those nitrogen-containing heterocyclic groups as disclosed in Japanese Patent O.P.I. Publication No. 115219/-1977; those urazole groups and hydantoin groups as disclosed in Japanese Patent Examined Publication No. 33410/1976; and those arylthio groups as disclosed in U.S. Pat. No. 3,227,554.

On the other hand, with the progress of silver halide light-sensitive photographic materials, the demand for improving the characteristics of couplers is becoming increasingly severe, and the above-mentioned two-equivalent-type yellow couplers are also demanded to be improved on the color developing efficiency. Therefore, various attempts have hitherto been made in designing coupler molecules; for example, there has been a proposal to improve the color formability by introducing an alkoxycarbonyl group or an N-substituted or unsubstituted alkylsulfonamido group or an arylsulfonamido group to the ballasting constituent. Such attempts, however, cannot be considered to have contributed adequately to the improvement.

Such yellow couplers have the disadvantage that the color formability thereof varies largely according to the pH of a color developer solution. The pH of the color developer solution generally varies to some extent according to the color developing agent, couplers, etc., contained therein, and particularly where a large quantity of color light-sensitive materials are processed running in an automatic processor, it is very difficult to have the pH maintained optimum due to the silver halide ions dissolved out of the light-sensitive material into the solution, accumulation of various additives in the solution, oxidation of the solution by the air, and the like. Accordingly, the development of an yellow coupler which is excellent in the color formability, wherein the color formability is hardly affected by the pH of a color developer solution, is urgently needed.

Further, in recent years, the demand for true color reproduction from the side of users who desire to have the real color of a subject vividly reproduced as it is in their own photographs has been increasing. As a concrete means to meet such a demand, reducing or dissolving the color turbidity of a formed dye as well as making the color tone of the dye clear may be feasible by developing such a coupler that the dye formed in the coupling reaction thereof with the oxidized product of a color developing agent has a sharp-cut wave-form-having visible absorption spectrum However, any research and development of such couplers from this point of view cannot be deemed to have been adequately made to date.

SUMMARY OF THE INVENTION

The present invention has been made in view of the above-mentioned circumstances. It is a first object of the present invention to provide a silver halide light-sensitive photographic material containing a novel two-equivalent-type yellow coupler which is excellent in the color formability and produces little or no fog.

It is a second object of the present invention to provide a silver halide light-sensitive photographic material containing a novel two-equivalent-type yellow coupler whose color formability is hardly affected by the pH of a color developer solution, thus giving a stable color image.

It is a third object of the present invention to provide a silver halide light-sensitive photographic material containing a novel two-equivalent-type yellow coupler which, in the reaction thereof with a color developing agent, forms a dye whose visible absorption spectrum is sharp-cut and which is excellent in the color reproducibility, giving a clear color image.

The above objects of the present invention are accomplished by a silver halide light-sensitive photographic material comprising a support having thereon at least one silver halide emulsion layer, the said at least one silver halide emulsion layer comprising a coupler having the following Formula [I]:

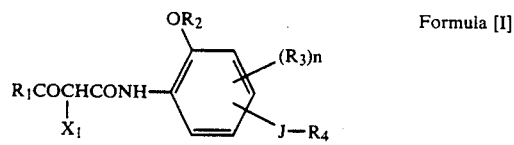

Formula [I]

wherein $R_1$ is an alkyl or cycloalkyl group: $R_2$ is an alkyl, cycloalkyl, acyl or aryl group; $R_3$ is a group substitutable to a benzene ring; n is zero or 1; $R_4$ is an organic group having 1 to 30 carbon atoms and containing one linkage group having a unit selected from the group of carbonyl and sulfonyl units; J is a

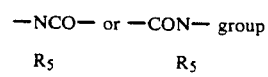

(wherein $R_5$ is a hydrogen atom, an alkyl, aryl or heterocyclic group); and $X_1$ is a group which can be split off during the coupling reaction with the oxidized product of a developing agent.

DETAILED DESCRIPTION OF THE INVENTION

The alkyl group represented by the $R_1$ in the above Formula [I] is, for example, a methyl group, ethyl group, isopropyl group, t-butyl group, dodecyl group, or the like. These alkyl groups represented by the $R_1$ further include those having a substituent. The substituent is, for example, a halogen atom, aryl group, alkoxy group, aryloxy group, alkylsulfonyl group, acylamino group, or hydroxy group.

The cycloalkyl group represented by the $R_1$ is a cyclopropyl group, cyclohexyl group, adamantyl group, or the like.

The $R_1$ is preferably a branched alkyl group.

In Formula [I], examples of the alkyl group and cycloalkyl group represented by the $R_3$ include the same exemplified groups as defined in the $R_1$, and the aryl group is, for example, a phenyl group. These alkyl, cycloalkyl and aryl groups represented by the $R_2$ also include those having the same substituents as in the $R_1$. The acyl group is, for example, an acetyl group, propionyl group, butyryl group, hexanoyl group, benzoyl group, or the like.

The $R_2$ is preferably an alkyl group or aryl group, and more preferably an alkyl group having 1 to 30 carbon atoms.

In Formula [I], the group substitutable to a benzene ring represented by the $R_3$ is a halogen atom (such as chlorine), an alkyl group (such as ethyl, i-propyl, t-butyl), an alkoxy group (such as methoxy), an aryloxy group (such as phenyloxy), an acyloxy group (such as methylcarbonyloxy, benzoyloxy), an acylamino group (such as acetamido, phenylcarbonylamino), a carbamoyl group (such as N-methylcarbamoyl, N-phenylcarbamoyl), an alkylsulfonamido group (such as ethylsulfonylamino), an arylsulfonamido group (such as phenylsulfonylamino), a sulfamoyl group (such as N-propylsulfamoyl, N-phenylsulfamoyl), an imido group (such as succinic acid imido, glutarimido), or the like. And n represents zero or 1.

In Formula [I], the $R_4$ is an organic group having 1 to 30 carbon atoms and containing one linkage group having a unit selected from the group of carbonyl and sulfonyl units.

The carbonyl unit-having group is an ester group, amido group, carbamoyl group, ureido group, urethane group, or the like. The sulfonyl unit-having group is a sulfone group, sulfonamido group, sulfamoyl group, aminosulfonamido group or the like.

The J represents

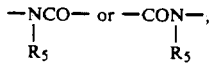

wherein $R_5$ is a hydrogen atom, or an alkyl, aryl or heterocyclic group.

The alkyl group represented by the $R_5$ is a methyl, ethyl, isopropyl, t-butyl, dodecyl or the like group. The aryl group represented by the $R_5$ is a phenyl or naphthyl group.

The alkyl or aryl group represented by the $R_5$ also includes those having a substituent. The substituent is not particularly restricted, and is typified by a halogen atom (such as chlorine), an alkyl group (such as ethyl, t-butyl), an aryl group (such as phenyl, p-methoxyphenyl, naphthyl), an alkoxy group (such as ethoxy, benzyloxy), an aryloxy group (such as phenoxy), an alkylthio group (such as ethylthio), an arylthio group (such as phenylthio), an alkylsulfonyl group (such as β-hydroxyethylsulfonyl), an arylsulfonyl group (such as phenylsulfonyl); an acylamino group such as, e.g., an alkylcarbonylamino group (e.g., acetamido), an arylcarbonylamino group (e.g., phenylcarbonylamino) or the like: a carbamoyl group such as one of those substituted by an alkyl or aryl group (preferably phenyl), including N-methylcarbamoyl group, N-phenylcarbamoyl group, etc.; an acyl group such as, e.g., an alkylcarbamoyl group such as acetyl, an arylcarbonyl group such as benzoyl, or the like: a sulfonamido group such as, e.g., an alkylsulfonylamino or arylsulfonylamino group, typified by methylsulfonylamino, benzenesulfonamido, etc.; a sulfamoyl group such as one of those substituted by an alkyl or aryl group (preferably phenyl), including N-methylsulfamoyl group, N-phenylsulfamoyl group, etc.; a hydroxy group, a nitrilo group, or the like.

In Formula [I], the $X_1$ is a group which can be split off during the coupling reaction with the oxidized product of a developing agent, the group being, for example, one of those groups having the following Formula [II] or [III]:

$$-OR_6 \qquad [II]$$

wherein $R_6$ is an aryl or heterocyclic group, including also those having a substituent.

wherein $Z_1$ is a group of nonmetallic atoms necessary to form a 5- or 6-member ring along with a nitrogen atom. The group of nonmetallic atoms necessary to form the cyclic ring include, e.g., $>C=O$, $-NH-$, $-N=$, $-O-$, $-S-$, $-SO_2-$, and the like.

The two-equivalent yellow coupler represented by the foregoing Formula [I] may be allowed to form a bis-type compound by linking at the $R_1$, $R_3$, or $R_4$ position.

The preferred ones as the two-equivalent yellow coupler of this invention are those having the following Formula [IV]:

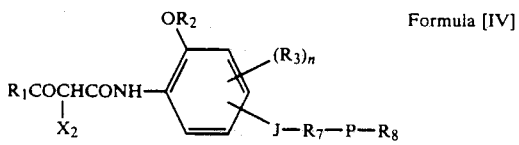

wherein $R_1$, $R_2$, $R_3$ and J are as defined in the $R_1$, $R_2$, $R_3$ and J of Formula [I]; n is zero or 1; $R_7$ is an alkylene group, an arylene group, an alkylene-arylene group, arylene-alkylene group, or $-A-V_1-B-$ (wherein A and B each is an alkylene, arylene, alkylene-arylene or arylene-alkylene group, and $V_1$ is a bivalent linkage group); $R_8$ is an alkyl group, a cycloalkyl group, an aryl group or a heterocyclic group; P is a linkage group having a carbonyl or sulfonyl unit; and $X_2$ is a group which can be split off during the coupling reaction with the oxidized product of a developing agent.

In Formula [IV], the alkyl group represented by the $R_7$ is, for example, a methylene group, ethylene group, propylene group, butylene group or hexylene group. These groups also include those having a substituent, such as those substituted by an alkyl group, e.g., methyl-methylene group, ethyl-ethylene group, 1-methyl-ethylene group, 1-methyl-2-ethyl-ethylene group, 2-decyl-ethylene group, 3-hexyl-propylene group, 1-benzyl-ethylene group, and those substituted by an aryl group, e.g., 2-phenyl-ethylene group, and 3-naphthyl-propylene group.

The arylene group represented by the $R_7$ is, for example, a phenylene or naphthylene group.

The alkylene-arylene group is, for example, a methylene-phenylene group or the like. The arylene-alkylene group is, for example, a phenylene-methylene group or the like.

The alkylene, arylene, alkylene-arylene or arylene-alkylene group represented by A or B is the same as the alkylene, arylene, alkylene-arylene or arylene-alkylene group represented by the $R_7$ of Formula [IV]. The bivalent linkage group represented by the $V_1$ is a group such as —O—, —S—, or the like.

The particularly preferred one out of the alkylene, arylene, alkylene-arylene and arylene-alkylene groups and —A—$V_1$—B— represented by the $R_7$ is the alkylene group.

In Formula [IV], the alkyl group represented by the $R_8$, is, for example, an ethyl group, butyl group, hexyl group, octyl group, dodecyl group, hexadecyl group, octadecyl group or the like. These alkyl groups each may be in the form of either straight-chain or branched-chain. The cycloalkyl group is a cyclohexyl group or the like. The aryl group is a phenyl or naphthyl group. The heterocyclic group is a pyridyl group or the like. These alkyl, cycloalkyl, aryl and heterocyclic groups represented by the $R_8$ also include those having a substituent. According to one preferred embodiment of the present invention, the total number of carbon atoms contained in each of the $R^7$ and $R^8$ is 4 to 30, and more preferably 7 to 30.

Examples of the substituent, although not particularly restricted, include those substituents as defined in the foregoing $R_5$, provided that those organic groups having dissociative hydrogen atoms having a pKa value of not more than 9.5 (e.g., phenolic hydrogen atom, etc.) are not acceptable as the substituent to the $R_8$.

In Formula [IV], the P is a linkage group having a carbonyl or sulfonyl unit, and preferably represents any one of the following groups shown in Group [V]:

Group [V]

—COO, (1)

—NCO—, (2)
   |
   R

—CON—, (3)
   |
   R

—NCON—, (4)
   |   |
   R   R'

—NCOO—, (5)
   |
   R

—SO₂—, (6)

-continued
Group [V]

—NSO₂, (7)
   |
   R

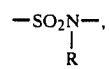
—SO₂N—, (8)
      |
      R

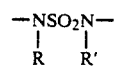
—NSO₂N—, (9)
   |    |
   R    R' wherein R and R' each is a hydrogen atom, an alkyl group, an aryl group or a heterocyclic group, provided that the R and R' may be either the same or different.

Examples of the group represented by the R or R' include those groups as defined in the $R_5$, and also include those having a substituent. The R and R' each is preferably a hydrogen atom.

In Formula [IV], the $X_2$ is a group splittable in the coupling reaction, and is preferably one of those groups having the following Formulas [VI] through [XII]:

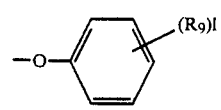

wherein $R_9$ is a carboxyl group, an ester group, an acyl group, an alkylsulfonyl group, an arylsulfonyl group, hydroxy group or a substituent similar to the group as defined in the foregoing $R_3$; and l is an integer of from 1 to 5, provided that the $R_9$ may be either the same or different when l is not less than 2.

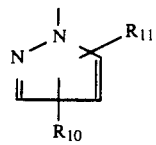

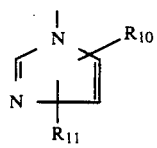

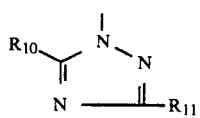

wherein $R_{10}$ and $R_{11}$ each is a hydrogen atom, a halogen atom, an alkyl, alkoxy, aryl, heterocyclic, carboxylate, amino, acylamino, alkylsulfonyl, arylsulfonyl, alkylsulfinyl, arylsulfinyl, alkylsulfonamido, arylsulfonamido or carboxylic acid group, provided that the $R_{10}$ and $R_{11}$ may be either the same or different and may also form a ring together.

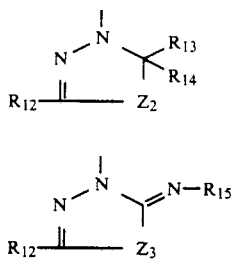

[X]

[XI]

wherein $Z_2$ and $Z_3$ each is a hetero atom, and $R_{12}$, $R_{13}$ and $R_{14}$ each represents similar groups to those as defined in the above $R_{10}$ and $R_{11}$; and $R_{15}$ is an alkyl, aryl, alkylcarbonyl, arylcarbonyl, alkylsulfonyl or arylsulfonyl group.

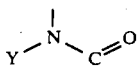

[XII]

wherein Y is a hetero atom (such as —NH—, —N=, —O—, —S—), a sulfonyl group, carbonyl group, or a carbon atom that is shown in

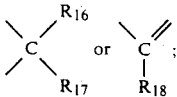

and $Z_4$ is a group of nonmetallic atoms necessary to form a 5- or 6-member ring along with —Y—N—CO—.

The above $R_{16}$, $R_{17}$ and $R_{18}$ each represents similar groups to those as defined in the foregoing $R_{10}$ and $R_{11}$ and may also form a ring along with part of the $Z_4$.

The two-equivalent yellow coupler having the foregoing Formula [IV] may be allowed to form a bis-type compound by linking at the position of the $R_1$ or $R_3$ or through a ballasting group.

The following are examples representative of the two-equivalent yellow coupler having Formula [I] to be used in this invention, but the invention is not limited to and by the following examples.

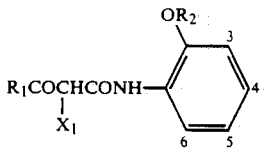

| NO. | $R_1$ | $R_2$ | $X_1$ | 3 |
|---|---|---|---|---|
| 1 | (t)C$_4$H$_9$— | —CH$_3$ | ![structure] | —H |
| 2 | (t)C$_4$H$_9$— | —CH$_3$ | ![structure with OC$_2$H$_5$] | —H |
| 3 | (t)C$_4$H$_9$— | —CH$_3$ | ![structure with N—C$_4$H$_9$(n)] | —H |
| 4 | (t)C$_4$H$_9$— | —CH$_3$ | ![structure] | —H |

-continued

| | | | | |
|---|---|---|---|---|
| 5 | (t)C₄H₉— | —CH₃ | ![structure: N-N ring with CHN, Cl substituent] | —H |
| 6 | (t)C₄H₉— | —CH₃ | ![structure: OC₄H₉(n), N-acyl imidazolidinedione with phenyl] | —H |
| 7 | (t)C₄H₉— | —C₃H₇(iso) | ![structure: OC₂H₅, acyl group with phenyl] | —H |
| 8 | (t)C₄H₉— | —CH₃ | —O—C₆H₄—SO₂—C₆H₄—O—CH₂—C₆H₅ | —H |
| 9 | (t)C₄H₉— | —C₁₂H₂₅(n) | —O—C₆H₄—SO₂—C₆H₄—OH | —H |
| 10 | (t)C₄H₉— | —C₁₈H₃₇(n) | ![structure: CONH-phenyl triazole] | —H |
| 11 | (t)C₄H₉— | —CH₃ | ![structure: hydantoin with N-C₆H₁₃(n) and N-phenyl] | —H |
| 12 | (t)C₄H₉— | —C₄H₉ | ![structure: imidazolidinedione with N-CH₂-phenyl] | —H |
| 13 | (t)C₄H₉— | —CH₃ | ![structure: hydantoin with N-CH₂-phenyl and N-phenyl] | —H |
| 14 | (t)C₄H₉— | —CH₃ | ![structure: N-N-CHN ring with Cl] | —H |

-continued
| | | | | |
|---|---|---|---|---|
| 15 | (t)C₄H₉— | —CH₃ | 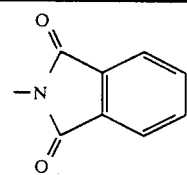 | —H |
| 16 | (t)C₄H₉— | —CH₃ | 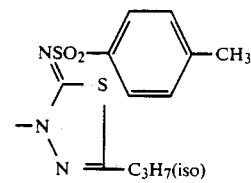 | —H |
| 17 | 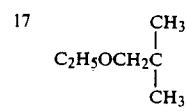 | —CH₃ | 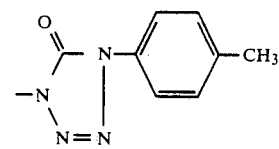 | —H |
| 18 | (t)C₄H₉— | —CH₃ | 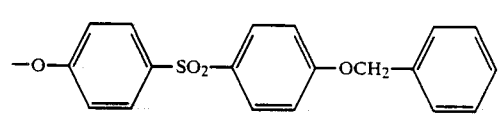 | —H |
| 19 | (t)C₄H₉— | —CH₃ | 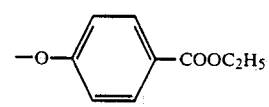 | —H |
| 20 | (t)C₄H₉— | —C₁₂H₂₅(n) | 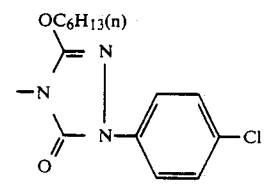 | —H |
| 21 | (t)C₄H₉— | —C₂H₅ | 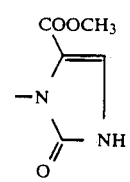 | —H |
| 22 | 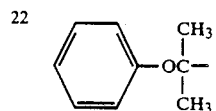 | —C₄H₉(n) | 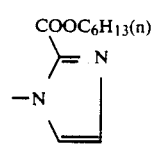 | —H |
| 23 | (t)C₅H₁₁ | —C₂H₅ | 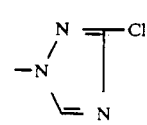 | —H |
| 24 | (t)C₄H₉— | —CH₃ | 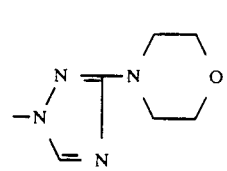 | —H |

-continued
| | | | | |
|---|---|---|---|---|
| 25 | (t)C$_4$H$_9$— | —C$_{16}$H$_{37}$(n) | 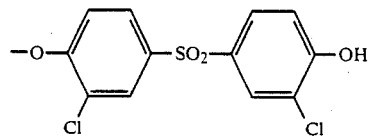 | —H |
| 26 | (t)C$_4$H$_9$— | —CH$_3$ | 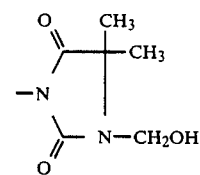 | —H |
| 27 | (t)C$_4$H$_9$— | —CH$_3$ | 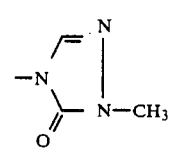 | —H |
| 28 | (t)C$_4$H$_9$— | —CH$_3$ | 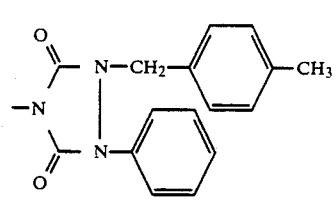 | —H |
| 29 | 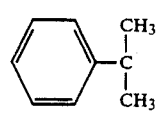 | —C$_{12}$H$_{25}$(n) | 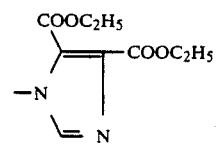 | —H |
| 30 | (t)C$_5$H$_{11}$— | —CH$_3$ | 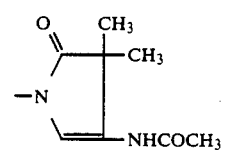 | —H |
| 31 | (t)C$_4$H$_9$— | —CH$_3$ | 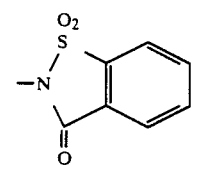 | —H |
| 32 | (t)C$_4$H$_9$— | —CH$_3$ | 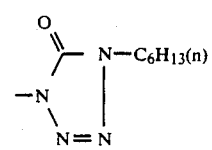 | —H |
| 33 | (t)C$_4$H$_9$— | —CH$_3$ | 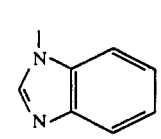 | —H |

-continued
| | | | | |
|---|---|---|---|---|
| 34 | (t)C$_4$H$_9$— | 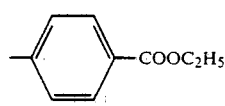 | 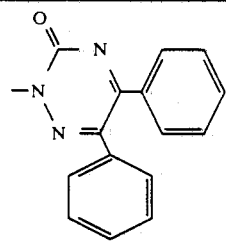 | —H |
| 35 | (t)C$_4$H$_9$— | —C$_4$H$_9$(n) | 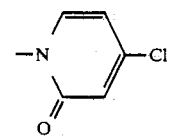 | —H |
| 36 | (t)C$_4$H$_9$— | —CH$_3$ | 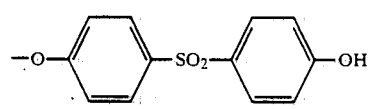 | —H |
| 37 | (t)C$_4$H$_9$— | 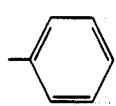 | 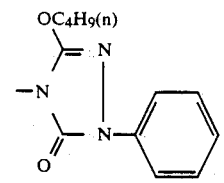 | —H |
| 38 | (t)C$_5$H$_{11}$— |  | 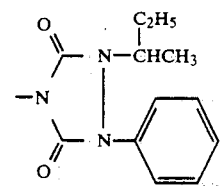 | —H |
| 39 | (t)C$_4$H$_9$— |  | 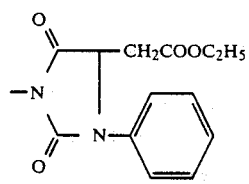 | —H |
| 40 | (t)C$_4$H$_9$— | —CH$_3$ | 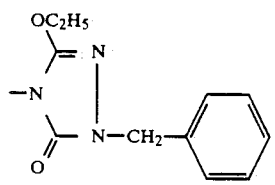 | —H |
| 41 | (t)C$_4$H$_9$— | —CH$_3$ | 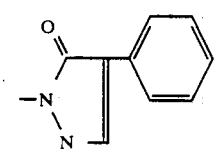 | —H |
| 42 | (t)C$_4$H$_9$— | —CH$_3$ | 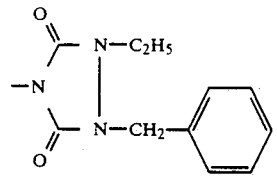 | —H |

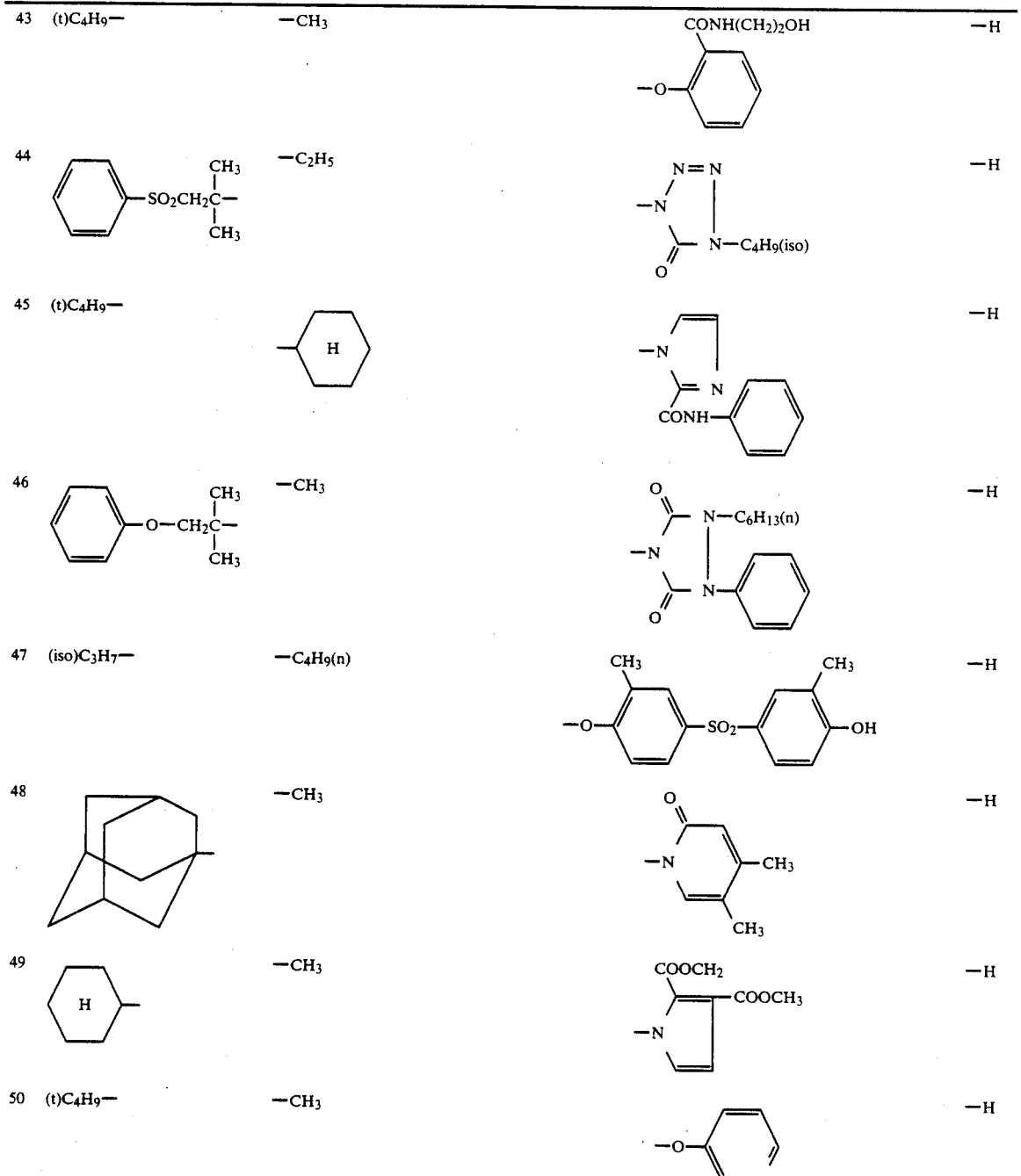

| | | | |
|---|---|---|---|
| 3 | —H | —NHCOCH(CH₃)CH₂SO₂C₁₂H₂₅(n) | —H |
| 4 | —H | —NHCO(CH₂)₂COO—C₆H₃(2-C₅H₁₁(t))(4-C₅H₁₁(t)) | —H |
| 5 | —H | —N(CH₂C₆H₅)—COCH(CH₃)CH₂SO₂C₁₈H₃₇(n) | —H |
| 6 | —H | —NHCO(CH₂)₂CON(C₂H₅)C₁₂H₂₅(n) | —H |
| 7 | —H | —CONH(CH₂)₃CONH—C₆H₄—C₁₂H₂₅(n) | —H |
| 8 | —H | —CONH—C₆H₄—NHCOC₁₂H₂₅(n) | —H |
| 9 | —H | —CONHCH(CH₃)CH₂SO₂C₂H₅ | —H |
| 10 | —H | —NHCOC(CH₃)(CH₃)CH₂SO₂C₄H₉(n) | —H |
| 11 | —H | —NHCOCH(CH₃)NHCO—C₆H₄—OC₁₂H₂₅(n) | —H |
| 12 | —H | —NHCOCH(C₁₂H₂₅)O—C₆H₄—SO₂NHC₄H₉(n) | —H |
| 13 | —H | —CONH(CH₂)₂NHSO₂C₁₂H₂₅(n) | —H |
| 14 | —H | —CONHCH(CH₃)CH₂SO₂CH₂CH(C₆H₁₃(n))C₈H₁₇(n) | —H |
| 15 | —H | —NHCOCH(C₁₂H₂₅(n))CH₂NHCOOC₂H₅ | —H |
| 16 | —H | —NHCOCH(CH₃)(CH₂)₂NHCO—C₆H₄—OC₁₂H₂₅(n) | —H |
| 17 | —H | —NHCO(CH₂)₁₀COOC₂H₅ | —H |

-continued

| | 21 | | 22 |
|---|---|---|---|
| 18 | —H | —CONH—(C6H4)—SO2NHC12H25(n) | —H |
| 19 | —H | —NHCO—(C6H4)—NHSO2CH2—(C6H3)(2-C5H11(t), 4-C5H11(t)) | —H |
| 20 | —H | —NHCO(CH2)2SO2NHCH2CH(C2H5)C4H9(n) | —H |
| 21 | —Cl | —NHCOC(CH3)2CH2SO2—(C6H3)(2-OC4H9(n), 5-C8H17(t)) | —H |
| 22 | —H | —NHCOCH(CH3)CH2CONH—(C6H4)—C12H25(n) | —H |
| 23 | —H | —NHCOCH(CH3)(CH2)2NHSO2—(C6H4)—OC6H13(n) | —H |
| 24 | —H | —NHCOC(CH3)2CH2O—(C6H4)—SO2—(C6H4)—OCH2—(C6H5) | —H |
| 25 | —H | —NHCO(CH2)2NHSO2N(CH3)(C6H5) | —H |
| 26 | —H | —CONH(CH2)4NHCO—(C6H3)(2-OC12H25(n), 5-CH3) | —H |
| 27 | —H | —CONHCH(C6H13(n))CH2SO2NHC12H25(n) | —H |
| 28 | —H | —CONH(CH2)3NHCOOC12H25(n) | —H |
| 29 | —H | —NHCO(CH2)3NHCONHCH2CH(C2H5)C4H9(n) | —H |
| 30 | —H | —CONHCH(C6H13(n))CH2CONH—(C6H4)—OC4H9(n) | —H |
| 31 | —H | —CONHCH(CH3)CH2N(CH3)SO2N(CH3)C16H33(n) | —H |

-continued

| | | | |
|---|---|---|---|
| 32 | —H | —NHCO(CH$_2$)$_3$NHCOCH$_2$CHC$_6$H$_{13}$(n)<br>                              \|<br>                         C$_8$H$_{17}$(n) | —H |
| 33 | —Cl | $\quad$ CH$_3$ $\qquad$ C$_{12}$H$_{25}$(n)<br>$\quad\quad\:$ \| $\qquad\qquad$ /<br>—NHCOCCH$_2$NHCON<br>$\quad\quad\:$ \| $\qquad\qquad$ \\<br>$\quad$ CH$_3$ $\qquad$ C$_2$H$_5$ | —H |
| 34 | —H | —CONHCH$_2$CHSO$_2$—C$_6$H$_4$—C$_{18}$H$_{37}$(n)<br>$\qquad\qquad\:$ \|<br>$\qquad\qquad\:$ C$_2$H$_5$ | —H |
| 35 | —NHCOCHSO$_2$NHC$_{12}$H$_{25}$(n)<br>$\quad\quad\:$ \|<br>$\quad\quad\:$ C$_{16}$H$_{33}$(n) | —Cl | —H |
| 36 | —Cl | —NHCO(CH$_2$)$_2$NHCO—C$_6$H$_4$—C$_{12}$H$_{25}$(n) | —H |
| 37 | —H | $\qquad\quad$ CH$_2$<br>$\qquad\quad$ /<br>—CONHCCH$_2$CONH—C$_6$H$_4$—OC$_{12}$H$_{25}$(n)<br>$\qquad\quad$ \\<br>$\qquad\quad$ CH$_2$ | —H |
| 38 | —OCH$_3$ | —NHCOCH(CH$_2$)$_2$NHSO$_2$—C$_6$H$_3$(OC$_{12}$H$_{25}$(n))(CH$_3$)<br>$\quad\quad\:\:$ \|<br>$\quad\quad\:\:$ C$_6$H$_5$ | —H |
| 39 | —H | $\qquad\quad$ CH$_3$<br>$\qquad\quad$ \|<br>—NHCOCCH$_2$NHCOOC$_8$H$_{17}$(n)<br>$\qquad\quad$ \|<br>$\qquad\quad$ CH$_3$ | —H |
| 40 | —H | $\qquad\quad$ CH$_3$<br>$\qquad\quad$ \|<br>—CONHC(CH$_2$)$_2$COO—C$_6$H$_4$—CH$_3$<br>$\qquad\quad$ \|<br>$\qquad\quad$ CH$_3$ | —H |
| 41 | $\qquad\qquad\qquad$ CH$_3$<br>$\qquad\qquad\qquad$ \|<br>—CONH(CH$_2$)$_4$NHSO$_2$CHC$_4$H$_9$(n) | —OCH$_3$ | —H |
| 42 | —H | —CONH—C$_6$H$_4$—SO$_2$NHC$_{12}$H$_{25}$(n) | —H |
| 43 | —H | $\qquad\quad$ CH$_3$<br>$\qquad\quad$ \|<br>—NHCOCCH$_2$SO$_2$NHC$_{12}$H$_{25}$(n)<br>$\qquad\quad$ \|<br>$\qquad\quad$ CH$_3$ | —H |
| 44 | —H | —NHCO(CH$_2$)$_3$CON—C$_6$H$_{13}$<br>$\qquad\qquad\qquad\quad\:$ \|<br>$\qquad\qquad\qquad\quad\:$ CH$_2$—C$_6$H$_5$ | —H |

-continued

| | | | |
|---|---|---|---|
| 45 | —H | —CONHCHCH$_2$SO$_2$—[3-OCH$_3$, 4-C$_8$H$_{17}$(t)-phenyl]<br>　　　　｜<br>　　　　C$_2$H$_5$ | —H |
| 46 | —H | —CONHCHCOOC$_{12}$H$_{25}$(n)<br>　　　　｜<br>　　　　C$_2$H$_5$ | —H |
| 47 | —H | —NHCOCHNHCOCH$_2$—[3-C$_5$H$_{11}$(t), 5-C$_5$H$_{11}$(t)-phenyl]<br>　　　　｜<br>　　　　CH$_3$ | —H |
| 48 | —H | —NHCO(CH$_2$)$_{10}$COOC$_2$H$_5$ | —H |
| 49 | —H | —CONH(CH$_2$)$_4$NHSO$_2$—[3-OC$_4$H$_9$(n), 4-C$_8$H$_{17}$(t)-phenyl] | —H |
| 50 | —H | —NHCO(CH$_2$)$_2$NHCONHCH$_2$O—[3-C$_5$H$_{11}$(t), 5-C$_5$H$_{11}$(t)-phenyl] | —H |

The yellow couplers of this invention can be synthesized in accordance with those conventional methods of the prior art. Typical synthesis examples in this invention will be given below:

Synthesis Example 1: Synthesis of Exemplified Coupler (3)

Twenty-eight point five grams of α-pivaloyl-2-methoxy-5-(α-methyl-β-dodecylsulfonylpropanamido)-acetanilide obtained from α-pivaloyl-2-methoxy-5-amino-acetanilide and α-methyl-β-dodecylsulfonyl-propionic acid chloride were dissolved into 150 ml of chloroform, and to this solution were added dropwise 4.2 ml of sulfuryl chloride under an iced water-cooling condition. After completion of the dropwise addition, the liquid was stirred for 20 minutes at room temperature. The reaction liquid was washed with water, then dehydrated by using magnesium sulfate, and then the solvent was distilled off.

Twelve point nine grams of the obtained residuum 1-butyl-2-phenylurazole and 8.0 g of potassium carbonate were added to 270 ml of ethyl acetate, and the mixture was refluxed with heating for a period of 3 hours. The undissolved substance was filtered off, and the reaction product was washed and then neutralized by a dilute sulfuric acid solution. After dehydration of it, the solvent was distilled off, and the thus obtained residuum was recrystallized in an n-hexane-ethyl acetate mixture solution. The structure of the product was confirmed by NMR, IR and Mass spectrum.

Yield: 24.9 g (62%)

| The results of elemental analysis (%): | | | | |
|---|---|---|---|---|
| | C | H | N | S |
| Calculated | 63.21 | 7.96 | 8.76 | 4.02 |
| Found | 63.00 | 7.92 | 8.74 | 4.00 |

Synthesis Example 2: Synthesis of Exemplified Coupler (4)

Synthesis of 3-[4-methoxy-3-nitrophenyl)carbamoyl] propionic acid-2,4-di-t-pentylphenyl Eighteen point zero grams of 4-methoxy-3-nitroaniline and 11.0 g of succinic anhydride were dissolved into 150 ml of ethyl acetate, and the mixture was refluxed with heating for 2 hours. The solvent was distilled off, and the residuum was recrystallized by adding 120 ml of methanol thereto.

Twenty-three point zero grams of the above-obtained 3-[(4-methoxy-3-nitrophenyl)-carbamoyl]-propionic acid, 20.0 g of 4-di-t-pentylphenol and 1.6 g of p-toluene-sulfonic acid were added to 200 ml of toluene, and the mixture was refluxed with heating for 5 hours. The solvent was distilled off, and the obtained residuum was dissolved in ethyl acetate, then washed with water and then dehydrated by magnesium sulfate, and after that the ethyle acetate was distilled off. The product was recrystallized in 180 ml of methanol, whereby an objective product was obtained.

Yield: 20.4g (39%)

(2) Synthesis of a Four-Equivalent Coupler

Twenty grams of the above-obtained 3-[(4-methoxy-3-nitrophenyl)-carbamoyl]-propionic acid-2,4-di-t-pentylphenyl were dissolved into 200 ml of ethyl acetate, and to this was added 1 g of 50% by wt/wt wet palladium carbon to hydrogenate it. After removing the palladium carbon, the solvent was distilled off.

The obtained residuum and 7.1 g of α-pivaloyl-ethyl acetate were added to 120 ml of xylene, and this mixture, with stirring, was refluxed with heating for a period of 8.5 hours while removing the alcohol being produced in the midst of the reflux. The whole xylene was distilled off, whereby an objective product was obtained. The obtained product, without being refined, was used for the subsequent process.
Yield: 23.8 g.

(3) Synthesis of Exemplified Coupler (4)

Twenty-three point zero grams of the above-obtained four-equivalent coupler were dissolved into 120 ml of chloroform, and to this solution were added dropwise 3.3 ml of sulfuryl chloride under an iced water-cooling condition. After completion of the dropwise addition, the mixture was stirred for 40 minutes. The reaction liquid was then washed and dehydrated by magnesium sulfate, and the solvent was distilled off, whereby 24.5 g of a residuum were obtained.

Eleven point six grams of 1-benzyl-2-phenylurazole and 6.3 g of potassium carbonate were added to 30 ml of ethyl acetate, and dissolved by stirring at room temperature. To this solution were added 100 ml of an ethyl acetate solution of 24.5 g of the above residuum dissolved therein, and this mixture was refluxed with heating for four hours. The undissolved substance was filtered off, and the filtrate was neutralized by dilute hydrochloric acid. After dehydration of the product by magnesium sulfate, the solvent was distilled off, and the residuum was recrystallized from 150 ml of methanol, whereby an objective product was obtained. The structure of the product was confirmed by NMR, IR and MS spectrum. Yield: 23.8 g (71%)

| The results of elemental analysis (%): | | | |
|---|---|---|---|
| | C | H | N |
| Calculated | 69.56 | 7.03 | 8.28 |
| Found | 69.81 | 6.98 | 8.25 |

Synthesis Example 3: Synthesis of Exemplified Coupler (18)

(1) Synthesis of N-dodecyl-4-aminobenzenesulfonamido

Twenty grams of 4-acetylaminophenylsulfonyl-chloride obtained from acetanilide and chlorosulfonic acid and 6.5 g of dodecylamine and 8.1 g of pyridine were added to 100 ml of acetonitrile, and the mixture was refluxed with heating for 3.5 hours. The solvent was distilled off under reduced pressure. 100 ml of ethyl acetate were added to this, and the organic phase was washed with a 5% potassium carbonate solution and a 1% hydrochloric acid solution, and then washed with water. After dehydration of the product by magnesium sulfate, the ethyl acetate was distilled off, whereby 17.7 g of a crude product was obtained.

Seventeen point five grams of the above-obtained 4-dodecyl-aminosulfonyl-acetanilide were added to 100 ml of concentrated hydrochloric acid, and the mixture was heated to 65° C. and stirred for 1 hour. After it foams, the stirring was continued with heating at 100° C. ±5° C. After that, the reaction liquid was poured into iced water, then extracted by 100 ml of ethyl acetate, and then washed with water. After dehydration of the liquid, the ethyl acetated was distilled off to thereby obtain a crude product, which was recrystallized from a mixture solvent of n-hexane and ethyl acetate in the ratio of 10:1. Yield: 10.9 g (36%)

(2) Synthesis of a Four-Equivalent Coupler

Ten point eight grams of N-dodecyl-4-aminobenzenesulfonamido were dissolved into 50 ml of ethyl acetate, and to this solution were added 50 ml of water and 2.6 g of potassium carbonate, and then the mixture was stirred vigorously. To this were added dropwise 30 ml of an ethyl acetate solution containing 7.8 g of 4-methoxy-3-nitrobenzoic acid chloride. After completion of the dropwise addition, the liquid was stirred for 10 minutes, and the organic phase was washed with a 5% potassium carbonate solution and dilute hydrochloric acid, and then washed with water. After dehydration of the product by magnesium sulfate, the solvent was distilled off, and the product was recrystallized from 100 ml of methanol. Yield: 15.1 g.

Fifteen grams of the above-obtained 4-dodecylaminosulfonyl-4-methoxy-3-nitrobenzanilide were dissolved into 150 ml of ethyl acetate, and to this solution was added 1 g of 50% by wt/wt wet palladium carbon to hydrogenate it. After removing the palladium carbon, the solvent was distilled off, and the obtained residuum and 5 g of α-pivaloyl-ethyl acetate were added to 100 ml of xylene, and the mixture, with stirring, was refluxed with heating for a period of 8 hours while distilling off the alcohol being produced in the midst of the reflux. The whole xylene was distilled off, and the obtained residuum was subjected to silica gel column chromatography, whereby an objective product was obtained. Yield: 11.5 g (59%).

(3) Synthesis of Exemplified Coupler (18)

Eleven point five grams of the above-obtained four-equivalent coupler were dissolved into 50 ml of chloroform, and to this solution were added dropwise 1.5 ml of sulfuryl chloride under an iced water-cooling condition. After completion of the dropwise addition, the reaction liquid was stirred for 40 minutes and washed with water, then dehydrated by magnesium sulfate, and then the solvent was distilled off.

Seven grams of the obtained residuum p-(p-benzyloxyphenylsulfonyl)-phenol and 1.50 g of potassium carbonate were added to 100 ml of acetone, and this mixture was refluxed with heating for a period of 8 hours. The undissolved substance was filtered off and then the acetone was distilled off, and the reaction product was dissolved in 100 ml of ethyl acetate, and then neutralized by dilute hydrochloric acid. The product was dehydrated by magnesium sulfate, and the thus obtained residuum was refined by silica gel column chromatography, and further recrystallized by 100 ml of methanol.

The structure of the obtained compound was confirmed by NMR, IR and MS spectrum Yield: 11.0 g (62%).

| The results of elemental analysis (%): | | | | |
|---|---|---|---|---|
| | C | H | N | S |
| Calculated | 65.45 | 6.66 | 4.40 | 6.72 |
| Found | 65.50 | 6.65 | 4.39 | 6.71 |

The above yellow couplers of this invention may be used alone or in combination of two or more of them.

Incorporation of any of the yellow couplers of this invention into a color photographic material can be carried out in the following manner: A single coupler or combined couplers are dissolved in a single high-boiling organic solvent or a mixture of high-boiling organic solvents having a boiling point of not less than 175° C. such as, for example, tricresyl phosphate, dibutyl phthalate, etc., or in a single low-boiling organic solvent or a mixture of low-boiling organic solvents such as, e.g., ethyl acetate, butyl propionate, etc., and the solution is then mixed with an aqueous gelatin solution containing a surface active agent. The mixture is subsequently emulsifiedly dispersed by a high-speed rotary mixer or colloid mill, and then directly added to a silver halide photographic emulsion, which is then coated on a support and then dried, or alternatively the above emulsifiedly dispersed liquid, after being set, is cut into small pieces and washed with water to thereby remove the low-boiling organic solvent therefrom, and then added to the emulsion to be coated on a support and then dried.

In general, the adding amount of the yellow coupler of this invention is preferably 10 to 300 g per mole of silver halide, but may be variously changed according to the purpose for which it is used.

The silver halide light-sensitive photographic material of this invention can be of any type and for any use. And the silver halide to be used in this invention may be, for example, silver chloride, silver bromide, silver iodide, silver chlorobromide, silver iodobromide, silver chloroiodobromide, or the like.

The silver halide light-sensitive photographic material of this invention, in order to form a multicolor image, may contain different other color forming couplers in addition to the yellow coupler of this invention.

The silver halide light-sensitive photographic material of this invention may contain arbitrary additives such as anticolor-stain agent, image stabilizer, hardening agent, plasticizer, polymer latex, formalin scavenger, mordant, development accelerator, development retarder, brightening agent, matting agent, solvent, antistatic agent, surface active agent, and the like.

The silver halide light-sensitive photographic material containing the yellow coupler of this invention can be improved on the durability of the yellow dye image thereof by incorporating a ultraviolet absorbing agent thereinto.

In this invention, any arbitrary processing procedure known to those skilled in the art may be applied; for example, such procedure steps as color developing, bleaching, fixing or bleach-fix, stabilizing, washing, stopping, and the like, may take place.

The silver halide light-sensitive photographic material containing the two-equivalent yellow coupler provided by this invention has a satisfactory color formability with its excellent sensitivity and maximum density, produces little or no fog, and is less affected by the pH of a color developer solution, thus providing a stable color image. In addition, the visible absorption spectrum of the formed dye produced in the reaction with a color developing agent is so sharp-cut as to give a color image excellent in the color reproducibility. The present invention will be illustrated in detail by the following examples. The embodiment of this invention is not limited to the examples.

EXAMPLE-1

As is shown in Table 1, $3.0 \times 10^{-2}$ mole each of the yellow couplers of this invention (indicated with the foregoing exemplified coupler numbers) and the following comparative yellow couplers was added to a mixture solution of dibutyl phthalate in a quantity corresponding to ¼ by weight of each coupler and a phenol compound in a quantity corresponding to ¼ by weight of each coupler and 40 ml of ethyl acetate, and dissolved by heating to 50° C. This solution was mixed with 10 ml of an aqueous 10% Alkanol B (alkylnaphthalene sulfonate, produced by DuPont) solution and 200 ml of an aqueous 5% gelatin solution, and the mixture was subjected to several-time emulsification operation by a colloid mill to thereby prepare a dispersed liquid.

This dispersed liquid was added to 500 ml of a gelatino-silver chlorobromide emulsion (containing 50 mole silver bromide), and the emulsion was coated on a polyethylene-laminated paper support so that the coated amount of silver chlorobromide was $0.25g/m^2$, and then dried, whereby silver halide light-sensitive photographic material Samples 1 through 17 were prepared. Each of these samples was exposed through an optical wedge in usual manner, and then processed in the following procedure by using the following processing liquids:

| [Processing Steps] | |
|---|---|
| Color developing at 38° C. | 3 min. 30 sec. |
| Bleach-fix at 33° C. | 1 min. 30 sec. |
| Washing at 25 to 30° C. | 3 min. |
| Drying at 75 to 80° C. | About 2 min. |
| [Color Developer (A)] | |
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-Methyl-4-amino-N-ethyl-N-(β-methane-sulfonamidoethyl)-aniline sulfate | 5.5 g |
| Brightening agent (4,4'-diaminostilbene-sulfonic acid derivative) | 1.0 g |
| Potassium hydroxide | 2.0 g |
| Water to made 1 liter, adjust the pH to 10.20. | |
| [Bleach-Fix Bath] | |
| Ferric-ammonium ethylenediaminetetraacetate dihydrated | 60.0 g |
| Ethylenediaminetetraacetic acid | 3.0 g |
| Ammonium thiosulfate (70% solution) | 100 ml |
| Ammonium sulfite (40% solution) | 27.5 ml |
| Add potassium carbonate or glacial acetic acid to adjust the pH to 7.1. | |
| Add water to make 1 liter. | |

The results and ΔλL20 of the dye image obtained in each sample by the above processing are as shown in Table 1, in which the ΔλL20, in the visible absorption spectrum of the dye image processed, means |λmax (maximum absorption wavelength) −λL20 (the wavelength on the longer wavelength side of the wavelength region showing an absorption accounting for 20% of the maximum absorption)|.

Phenol Compound

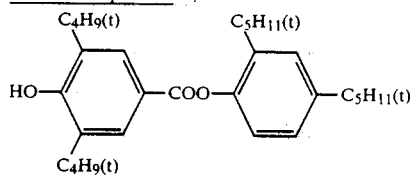

Comparative Couplers

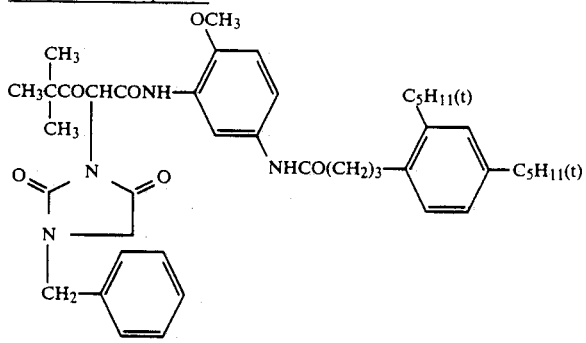
(A)

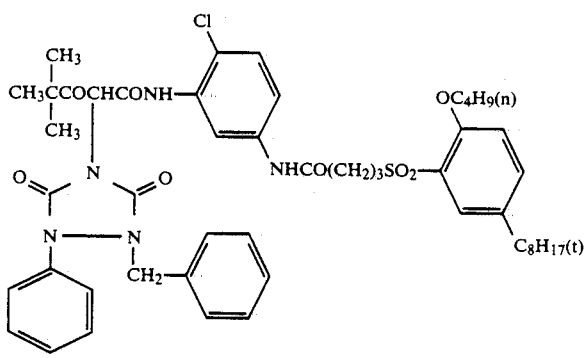
(B)

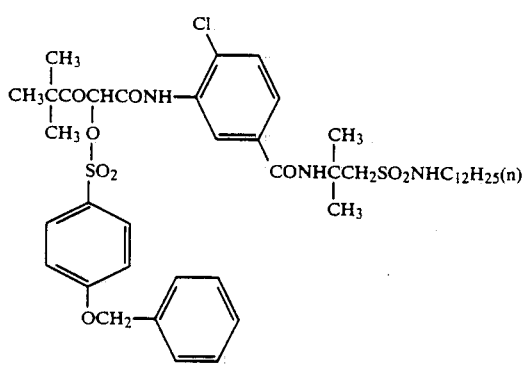
(C)

TABLE 1

| Sample No. | Coupler No. | Fog | Sensitivity | Maximum density | ΔλL20 |
|---|---|---|---|---|---|
| 1 (Invention) | 1 | 0.02 | 117 | 2.53 | 85 |
| 2 (Invention) | 2 | 0.02 | 118 | 2.56 | 85 |
| 3 (Invention) | 3 | 0.02 | 124 | 2.68 | 85 |
| 4 (Invention) | 6 | 0.02 | 116 | 2.51 | 86 |
| 5 (Invention) | 7 | 0.03 | 119 | 2.61 | 85 |
| 6 (Invention) | 8 | 0.03 | 118 | 2.57 | 85 |
| 7 (Invention) | 9 | 0.02 | 122 | 2.66 | 84 |
| 8 (Invention) | 11 | 0.02 | 115 | 2.52 | 85.5 |
| 9 (Invention) | 12 | 0.03 | 120 | 2.67 | 84.5 |
| 10 (Invention) | 13 | 0.03 | 121 | 2.62 | 86 |
| 11 (Invention) | 15 | 0.03 | 119 | 2.61 | 86 |
| 12 (Invention) | 18 | 0.03 | 123 | 2.63 | 85.5 |
| 13 (Invention) | 19 | 0.03 | 122 | 2.67 | 86 |
| 14 (Invention) | 28 | 0.02 | 117 | 2.55 | 85 |
| 15 (Comparative) | A | 0.03 | 100 | 2.21 | 86 |
| 16 (Comparative) | B | 0.04 | 107 | 2.32 | 90 |
| 17 (Comparative) | C | 0.04 | 104 | 2.30 | 91 |

Note:
The values shown in the 'Sensitivity' column are relative sensitivities to the Sample 15's sensitivity regarded as 100.

It is apparent from Table 1 that any of the couplers of this invention is excellent in the color formability in connection with the sensitivity and maximum density, produces little or no fog, and also excellent in the sharp-cut waveform of the visible absorption spectrum of the formed dye as compared to the comparative couplers, Also, it is understood that Comparative Coupler (A), although its spectral waveform is sharp-cut, is inferior in the color formability to the couplers of this invention.

EXAMPLE-2

As is shown in Table 2, 0.1 mole each per mole of silver of the yellow couplers of this invention and the following comparative couplers was taken to be added to a mixture of dioctyl phthalate as a high-boiling solvent in the same weight as that of each coupler and ethyl acetate in a weight thrice that of each coupler, and was completely dissolved in the mixed solvent by being heated to 60° C. This solution was mixed with 1200 ml of an aqueous 5% gelatin solution containing 120 ml of a Alkanol B (alkylnaphthalene sulfonate, produced by DuPont) solution, and then dispersed by an ultrasonic disperser to thereby obtain a emulsified product. After that, this dispersed liquid was added to 4 kg of a blue-sensitive silver iodobromide emulsion (containing 7 mole% silver iodide), and to this was further added 120 ml of a 2% 1.2-bis(vinylsulfonyl)ethane solution (water:methanol=1:1) as a hardening agent, and this liquid was then coated on a subbed transparent polyester base support so that the coated amount of silver iodobromide was 15 mg/100dm$^2$, and then dried, whereby stably coated layer-having silver halide light-sensitive photographic material Samples 18 through 38 were prepared.

Each of these samples was exposed through an optical wedge in usual manner, and then processed in the following procedure, using the following compositions-having processing liquids:

| [Processing Steps] | |
|---|---|
| Color developing at 38° C. | 3 min. 15 sec. |
| Bleaching at 38° C. | 6 min. 30 sec. |
| Washing at 38° C. | 3 min. 15 sec. |
| Fixing at 38° C. | 6 min. 30 sec. |
| Washing at 38° C. | 3 min. 15 sec. |
| Stabilizing at 38° C. | 1 min. 30 sec. |
| Drying | |
| [Color Developer (B)] | |
| 4-Amino-3-methyl-N-ethyl-N-(β-hydroxy-ethyl)-aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Trisodium nitrilotriacetate, monohydrated | 2.5 g |
| Potassium hydroxide | 1.0 g |
| Water to make 1 liter. Use an aqueous potassium hydroxide solution to adjust the pH to 10.0. | |
| [Bleacher Bath] | |
| Iron-ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| Water to make 1 liter. Use aqueous ammonia to adjust the pH to 6.0. | |
| [Fixer Bath] | |
| Ammonium thiosulfate | 175.0 g |
| Anhydrous sodium sulfite | 8.5 g |
| Sodium metasulfite | 2.3 g |
| Water to make 1 liter. Use acetic acid to adjust the pH to 6.0. | |
| [Stabilizer Bath] | |
| Formalin (aqueous 37% solution) | 1.5 ml |
| Koniducks (produced by Konishiroku Photo Industry Co., Ltd.) | 7.5 ml |
| Water to make 1 liter. | |

Comparative Coupler (D)

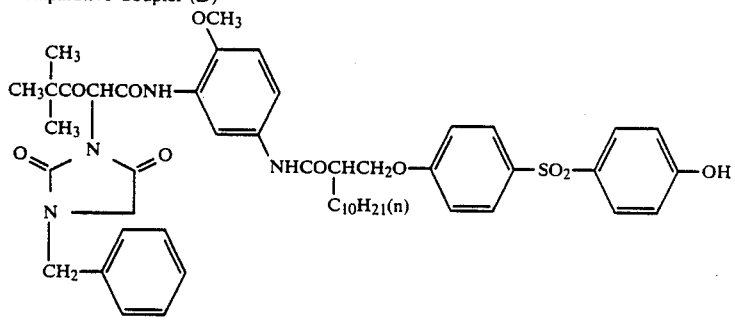

[Color Developer (C)] was prepared in the same manner as in the [Color Developer (B)] except that the former's pH was adjusted to 9.7.

The results of the respective samples' dye images obtained by the above procedure are given in Table 2.

TABLE 2

| Sample No. | Coupler No. | Developer (B) | | | Developer (C) | | |
|---|---|---|---|---|---|---|---|
| | | Fog | Sensi-tivity | Maximum density | Fog | Sensi-tivity | Maximum density |
| 18 (Invention) | 4 | 0.03 | 121 | 2.68 | 0.03 | 113 | 2.51 |
| 19 (Invention) | 6 | 0.03 | 120 | 2.64 | 0.02 | 110 | 2.48 |
| 20 (Invention) | 7 | 0.04 | 123 | 2.69 | 0.04 | 114 | 2.53 |
| 21 (Invention) | 8 | 0.04 | 121 | 2.66 | 0.03 | 111 | 2.47 |
| 22 (Invention) | 10 | 0.03 | 129 | 2.81 | 0.03 | 118 | 2.62 |
| 23 (Invention) | 13 | 0.03 | 127 | 2.75 | 0.03 | 116 | 2.58 |
| 24 (Invention) | 14 | 0.04 | 128 | 2.79 | 0.03 | 117 | 2.59 |
| 25 (Invention) | 16 | 0.03 | 119 | 2.61 | 0.03 | 110 | 2.47 |
| 26 (Invention) | 20 | 0.04 | 128 | 2.76 | 0.03 | 118 | 2.60 |
| 27 (Invention) | 23 | 0.04 | 127 | 2.76 | 0.04 | 117 | 2.59 |
| 28 (Invention) | 24 | 0.04 | 125 | 2.72 | 0.03 | 114 | 2.48 |
| 29 (Invention) | 25 | 0.04 | 125 | 2.73 | 0.04 | 113 | 2.52 |
| 30 (Invention) | 27 | 0.04 | 126 | 2.74 | 0.04 | 118 | 2.61 |
| 31 (Invention) | 31 | 0.04 | 122 | 2.70 | 0.03 | 111 | 2.48 |
| 32 (Invention) | 33 | 0.04 | 120 | 2.63 | 0.03 | 110 | 2.47 |
| 33 (Invention) | 40 | 0.04 | 122 | 2.68 | 0.04 | 113 | 2.53 |
| 34 (Invention) | 50 | 0.04 | 126 | 2.73 | 0.03 | 116 | 2.56 |
| 35 (Comparative) | A | 0.04 | 100 | 2.29 | 0.03 | 83 | 1.88 |
| 36 (Comparative) | B | 0.05 | 106 | 2.38 | 0.04 | 86 | 1.94 |
| 37 (Comparative) | C | 0.05 | 103 | 2.35 | 0.05 | 85 | 1.92 |
| 38 (Comparative) | D | 0.06 | 112 | 2.48 | 0.05 | 88 | 1.96 |

Note:
The values in the 'Sensitivity' column are relative sensitivities to the Sample 35's sensitivity obtained when processed in Developer (B), which is regarded as 100.

As is apparent from Table 2, any of the couplers of this invention is excellent in the color formability in connection with the sensitivity and maximum density, produces little or no fog, and also excellent in the color formability at a low pH, so that the color formability is hardly affected by changes in the pH, as compared to the comparative couplers. It is also understood that Comparative Coupler (D), although excellent in the color formability at a usual pH, produces a large fog, and is largely affected by changes in the pH as compared to any of the couplers of this invention.

EXAMPLE-3

A both-side-polyethylene-coated paper support was subjected to corona discharge treatment, and then on the support were coated in order from the support side the following seven layers, whereby a multilayer color photographic paper Sample 39 was prepared.

Layer 1: A layer containing 1.5 g of gelatin, 0.33 g (silver equivalent) of a blue-sensitive silver chlorobromide emulsion (containing 85 mole% silver bromide, average grain size 0.65 μm), and 0.25 g of dioctyl phthalate into which are dissolved $1.1 \times 10^{-3}$ mole of Exemplified Yellow Coupler (1) and 0.015 g of the following HQ-1.

Layer 2: A layer containing 1.0 g of gelatin and 0.06 g of dioctyl phthalate into which is dissolved 0.09 g of HQ-1.

Layer 3: A layer containing 1.3 g of gelatin, 0.27 g (silver equivalent) of a green-sensitive silver chlorobromide emulsion (containing 50 mole% silver bromide, average grain size 0.45 μm), 0.2 g of dioctyl phthalate into which are dissolved $0.59 \times 10^{-3}$ mole of the following Magenta Coupler M-1 and 0.015 g of HQ-1, and 0.15 g of the following Antiirradiation Dye AID-1.

Layer 4: A layer containing 1.5 g of gelatin and 0.6 g of dioctyl phthalate into which are dissolved 0.8 g of Ultraviolet Absorbing Agent UV-1 and 0.04 g of HQ-1.

Layer 5: A layer containing 1.3 g of gelatin, 0.3 g (silver equivalent) of a red-sensitive silver chlorobromide emulsion (containing 50 mole%, average grain size 0.35 μm), and 0.2 g of dioctyl phthalate into which are dissolved $0.75 \times 10^{-3}$ mole of the following Cyan Coupler C-1 and 0.05 g of HQ-1.

Layer 6: A layer containing 1.0 g of gelatin and 0.015 g of dioctyl phthalate into which are dissolved 0.4 g of Ultraviolet Absorbing Agent UV-2 and 0.01 g of HQ-1.

Layer 7: A layer containing 1.0 g of gelatin and 0.015 g of the following Filter Dye AID-2.

Samples 40 through 56 were then prepared in the same manner as in Sample 39 except that the coupler of the Layer 1 of Sample 39 was replaced by those couplers as given in Table 3.

Each of these samples was exposed through an optical wedge to blue, green and red lights separately, and then processed in the same manner as in Example-1 except that the [Color Developer (A)] in Example-1, [Color Developer (D)] which is the same as [Color Developer (A)] except that the pH is adjusted to 10.0, [Color Developer (E)] which is also the same except that the pH is adjusted to 9.8, and [Color Developer (F)] which is also the same except that the pH is adjusted to 10.4, were prepared and used.

The results are as given in Table 3.

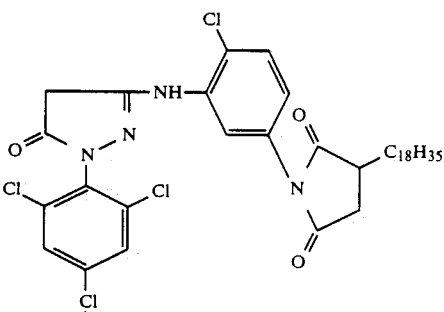

M-1

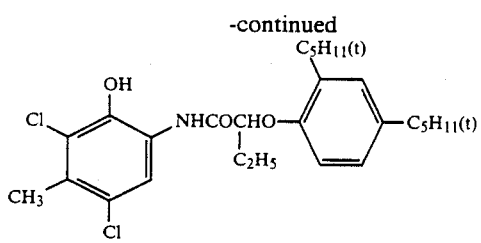
C-1
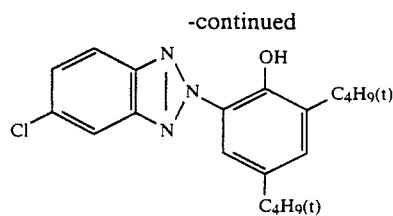
UV-2

TABLE 3

| Sample No. | Coupler No. | Maximum density (yellow) | | | |
|---|---|---|---|---|---|
| | | Developer (A) | Developer (D) | Developer (E) | Developer (F) |
| 39 (Invention) | 1 | 2.46 | 2.32 | 2.21 | 2.56 |
| 40 (Invention) | 2 | 2.50 | 2.38 | 2.26 | 2.59 |
| 41 (Invention) | 3 | 2.61 | 2.51 | 2.38 | 2.70 |
| 42 (Invention) | 6 | 2.43 | 2.29 | 2.17 | 2.53 |
| 43 (Invention) | 7 | 2.52 | 2.40 | 2.27 | 2.63 |
| 44 (Invention) | 8 | 2.49 | 2.34 | 2.21 | 2.60 |
| 45 (Invention) | 9 | 2.59 | 2.45 | 2.28 | 2.70 |
| 46 (Invention) | 11 | 2.46 | 2.35 | 2.23 | 2.58 |
| 47 (Invention) | 12 | 2.60 | 2.49 | 2.35 | 2.69 |
| 48 (Invention) | 13 | 2.55 | 2.42 | 2.28 | 2.67 |
| 49 (Invention) | 15 | 2.54 | 2.42 | 2.25 | 2.66 |
| 50 (Invention) | 18 | 2.56 | 2.44 | 2.29 | 2.69 |
| 51 (Invention) | 19 | 2.59 | 2.48 | 2.33 | 2.70 |
| 52 (Invention) | 28 | 2.47 | 2.36 | 2.22 | 2.59 |
| 53 (Comparative) | A | 2.12 | 1.84 | 1.54 | 2.28 |
| 54 (Comparative) | B | 2.22 | 1.95 | 1.67 | 2.35 |
| 55 (Comparative) | C | 2.22 | 1.91 | 1.64 | 2.32 |
| 56 (Comparative) | D | 2.42 | 2.15 | 1.84 | 2.58 |

It is also apparent from the results in Table 3 that each of the couplers of this invention is largely improved on the dependence of the color formability indicated with the maximum density upon the pH.

EXAMPLE-4

Each of Samples 39 through 52, 54 and 55 obtained in Example-3 was exposed through a negative film bearing an image composed of seven sample colors —red, orange, yellow, green, blue, indigo-blue and purple, and then processed in the same manner as in Example-1 to thereby obtain an image.

These processed image samples were compared visually. As a result, the image samples obtained from Samples 39 through 52 containing the yellow couplers of this invention were excellent in the color reproducibility, particularly in the reproducibility of the red, orange and green portions, as compared to Samples 54 and 55 containing the comparative couplers.

What is claimed is:

1. A silver halide light-sensitive photographic material comprising a support and, provided thereon, at least one silver halide emulsion layer containing a dye-forming coupler wherein said dye-forming coupler is one represented by Formula [IV]:

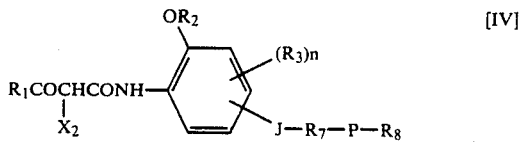

[IV]

wherein, $R_1$ is an alkyl group or a cycloalkyl group; $R_2$ is an alkyl group, a cycloalkyl group, an acyl group or an aryl group; $R_3$ is a group which is substitutable to a benzene ring, n is 0 or 1; J is a

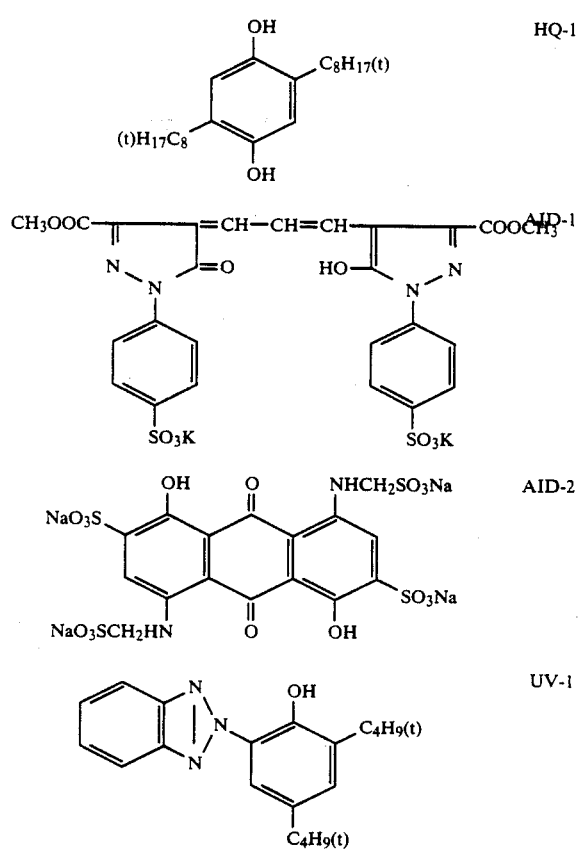

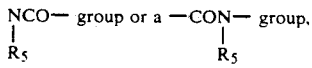

wherein $R_5$ is a hydrogen atom, an alkyl group, an aryl group or a heterocyclic group; $R_7$ is an unsubstituted alkylene group that can be branched or unbranched; $R_8$ is an alkyl group, a cycloalkyl group, an aryl group or a heterocyclic group $X_2$ is a group capable of being split off upon reaction with the oxidation product of a color developing agent; and P is a linkage group selected from the group consisting of a —COO— group, a —SO—$_2$ group, a —NCO— group, a —CON— group,

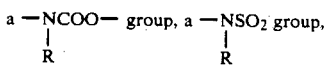

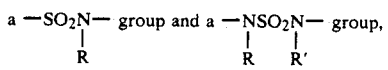

in which R and R' each is independently a hydrogen atom, an alkyl group, an aryl group or a heterocyclic group.

2. The silver halide light-sensitive photographic material of claim 1, wherein said R and R' are hydrogen atoms.

3. The silver halide light-sensitive photographic material of claim 1, wherein said $X_2$ is a group represented by one of Formulae [VI] through [XII]:

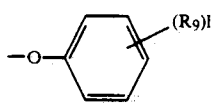

in which $R_9$ is a carboxyl group, an ester group, an acyl group, an alkylsulfonyl group, an arylsulfonyl group, a hydroxyl group or one of those groups as defined in $R_3$, 1 is an integer of 1 to 5, provided that when 1 is 2 or more $R_9$ may be either the same or different groups,

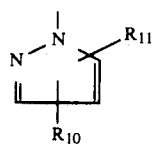

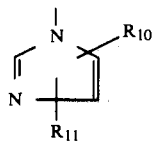

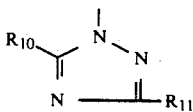

in which $R_{10}$ and $R_{11}$ each is independently a hydrogen atom, a halogen atom, an alkyl group, an alkoxy group, an aryl group, a heterocyclic group, a carboxylate group, an amino group, an acylamino group, an alkylsulfonyl group, an arylsulfonyl group, an alkylsulfinyl group, an arylsulfinyl group, an alkylsulfonamido group, an arylsulfonamido group and a carboxyl group, provided that $R_{10}$ and $R_{11}$ may cooperatively form a ring;

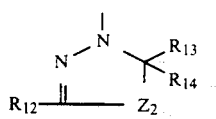

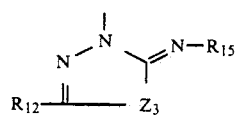

in which $Z_2$ and $Z_3$ each is independently a heterocyclic group; $R_{12}$, $R_{13}$ and $R_{14}$ represent independently the same groups as defined for $R_{10}$ and $R_{11}$; and $R_{15}$ is an alkyl group, an aryl group, an alkylcarbonyl group, an arylcarbonyl group, an alkylsulfonyl or an arylsulfonyl group;

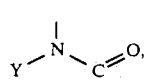

in which Y is a hetero atom, a —NH— group, a sulfonyl group, a carbonyl group,

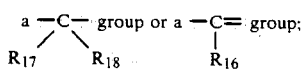

$Z_4$ is a group of atoms necessary to complete a 5-member or a 6-member ring; and $R_{16}$, $R_{17}$ and $R_{18}$ represent independently the same groups as defined for $R_{11}$, provided that at least one of $R_{16}$, $R_{17}$ and $R_{18}$ may form a ring with a portion of $Z_4$.

4. The silver halide light sensitive photographic material of claim 3, wherein $R_3$ is a halogen atom, ethyl, i-propyl, t-butyl, methoxy, phenyloxy, methylcarbonyloxy, benzoyloxy, acetamido, phenylcarbonylamino, N-methylcarbamoyl, N-phenylcarbamoyl, ethylsulfonylamino, phenylsulfonylamino, N-propylsulfamoyl, N-phenylsulfamoyl, succinic acid imido, glutarimido;

$R_5$ is a substituted or unsubstituted group selected from the group consisting of methyl, ethyl, isopropyl, t-butyl, dodecyl, phenyl and naphthyl, and wherein the substituents are halogen ethyl, t-butyl, phenyl, p-methoxyphenyl, naphthyl, ethoxy, benzyloxy, phenoxy, ethylthio, phenylthio, β-hydroxyethylsulfonyl, phenylsulfonyl; acetamido, phenylcarbonylamino, N-methylcarbamoyl group, N-phenylcarbamoyl group, acetyl, benzoyl, methylsulfonylamino, benzenesulfonamido, N-methylsulfamoyl group, N-phenylsulfamoyl group; a hydroxy group; a nitrilo group; and $R_7$ is a methylene group, ethylene group, propylene group, butylene group or hexylene group.

5. The silver halide light-sensitive material of claim 1 wherein
$R_5$ is hydrogen or alkyl.

6. The silver halide light-sensitive material of claim 5 wherein $R_5$ is hydrogen.

7. The silver halide light-sensitive material of claim 5 wherein $R_5$ is methyl, ethyl, isopropyl, t-butyl or dodecyl.

8. The silver halide light-sensitive material of claim 1 wherein $R_5$ is phenyl or naphthyl.

* * * * *